_United States Patent_ [19]

Sun et al.

[11] 4,439,347

[45] Mar. 27, 1984

[54] PHOTOMETRIC ACCURACY AND LINEARITY TEST SOLUTION

[75] Inventors: Lilla S. Sun, Seal Beach; John C. Anderson, Burbank, both of Calif.

[73] Assignee: Beckman Instruments, Inc., Fullerton, Calif.

[21] Appl. No.: 330,974

[22] Filed: Dec. 15, 1981

[51] Int. Cl.³ .................... G01N 31/00; G01N 33/00; G01D 18/00; G01B 13/00
[52] U.S. Cl. .................... 252/408.1; 436/8; 436/19; 250/252.1
[58] Field of Search ............ 252/408.1; 250/252.1; 436/8, 19

[56] References Cited

PUBLICATIONS

Rand, "Practical Spectrophotometric Standards," _Clin. Chem._, pp. 839–863, vol. 15, No. 9, 1969.
Lucas et al., "Spectrophotometric Standards in the Clinical Laboratory," _American Laboratory_, v. 9 (11), pp. 77–89.
Merck Index, 8th Ed., p. 67, "Ammonium Cobaltous Sulfate", 1968.
H. Remy, Tretise on Inorganic Chemistry, 1956, vol. 2, pp. 300–301, Elsevier Publishing Co.
Frings, "Convenient Method for Checking Detector Response of Spectrophotometers at Three Wavelengths," _Clin. Chem._, vol. 22, No. 1, 1976.
Frings, "Calibration and Monitoring of Spectrometers and Spectrophotometers," _Clin. Chem._, vol. 25, No. 6, 1979.

_Primary Examiner_—Teddy S. Gron
_Assistant Examiner_—Catherine S. Kilby
_Attorney, Agent, or Firm_—R. J. Steinmeyer; J. E. Vanderburgh; R. S. Frieman

[57] ABSTRACT

A solution of the type comprising cobalt ammonium sulfate and sulfuric acid. The solution is characterized in that it comprises from about 0.020 to about 0.040 N $H_2SO_4$.

Also, a method for checking the linearity of response of a spectrometer or spectrophotometer. The method is of the type comprising measuring absorbance (A) or percent transmittance (%T) of a solution versus a blank at a known wavelength. The method is characterized in that the above solution is employed therein.

In addition, a method for checking photometric accuracy of a spectrometer or spectrophotometer. The method is of the type comprising measuring A or %T of a solution at a specific wavelength. The method is characterized in that the above solution is employed therein.

3 Claims, No Drawings

PHOTOMETRIC ACCURACY AND LINEARITY TEST SOLUTION

BACKGROUND OF THE INVENTION

1. Field of the Invention

This invention relates to a test solution and, more particularly to a solution which can be used to check photometric accuracy and linearity.

2. Description of the Prior Art

Frings et al. (1) report that the percentage of quantitative analyses performed in the clinical laboratory that involve spectrophotometry or colorimetry was estimated in 1969 to be possibly more than 95% (2). Most laboratories continue to rely heavily upon spectrometer or spectrophotometers for the majority of their analyses. Maintenance of properly functioning spectrometers and spectrophotometers is an obvious prerequisite to the assurance of accurate analytical results. Moreover, the increased regulation of clinical laboratory by governmental and professional agencies mandates that laboratory personnel periodically verify that a given spectrometer or spectrophotometer is functioning properly. By periodically inspecting spectrometric and spectrophotometric functions, subtle or gradual degradations in performance can be detected before they significantly affect analytical results. As a minimum, these inspections should include, inter alia, checks for photometric accuracy and linearity of detector response.

With respect to linearity of detector response, a properly functioning spectrometer or spectrophotometer must exhibit a linear relationship between the radiant energy absorbed and the instrument readout (3). Instrument linearity is a prerequisite for spectrometric and spectrophotometric accuracy as well as for analytical accuracy. Several methods have been proposed for certifying that the detector response of spectrometers and spectrophotometers is linear over the range of wavelengths used (2–5).

The most common method for certifying linearity of detector response is through the use of solutions of compounds known to follow Beer's Law. Although it has been stated that the fulfillment of Beer's Law is a necessary but not sufficient condition for spectrometer and spectrophotometer linearity (4), the alternative procedures suggested for checking linearity are so elaborate and tedious that the use of solutions remain the most practical procedure available in the clinical laboratory.

The Subcommittee on Spectrophotometry of the Standards Committee of the American Association for Clinical Chemistry recommended in 1969 that photometric linearity be checked by preparing dilutions of appropriate compounds (2). Compounds reported for this purpose (2, 5) include oxyhemoglobin at 415 nm, p-nitrophenol at 405 nm, cobalt ammonium sulfate at 512 nm, copper sulfate at 650 nm and cyanmethemoglobin at 540 nm.

With respect to photometric accuracy, when performing analyses that do not use chemical standards, absorbance accuracy is essential. An absorbance standard (3) should have constant, stable absorbance over a suitable wavelength range that is insensitive to the spectral bandwidth of the instrument and to variations in the geometry of the light beam; and it should be easy to use, readily available, and inexpensive.

In general, linearity of detector response involves measuring absorbance (A) or percent transmittance (%T) of solutions having four different concentrations of cobalt ammonium sulfate present therein at a given wavelength. The concentration of cobalt ammonium sulfate present in each solution differs in an arithmetic progression advancing from 0 concentration of cobalt ammonium sulfate to a desired upper limit present in the fourth solution.

In general, the photometric accuracy technique involves measuring A or %T of the photometric accuracy test solution at a given wavelength.

A solution of cobalt ammonium sulfate and sulfuric acid (0.37 normal $H_2SO_4$) has been employed to check linearity of the detector response as well as photometric accuracy. The amount of sulfuric acid present in these solutions is relatively caustic, and, therefore, requires special caution with regard to shipping and handling and, in addition, causes excessive wear on those parts of the instrument with which it comes in contact (Rand, Clin. Chem., 15 pp. 839–863(1969)).

Accordingly, it would be desirable to use a cobalt ammonium sulfate solution in a form devoid of these attendant disadvantages.

SUMMARY OF THE INVENTION

In accordance with the present invention, there is provided a novel solution. More particularly, the solution of the instant invention is of the type comprising cobalt ammonium sulfate and sulfuric acid. The solution is characterized in that the sulfuric acid is present therein an amount of from about 0.020 to about 0.040 normal (N).

This normality of sulfuric acid is sufficiently dilute to render it non-caustic. Accordingly, the solution of this invention can be easily handled, shipped, and, in addition, does not cause any deterioration in any instrument parts with which it comes in contact.

In addition, the instant invention also comprises an improved method for checking the linearity of response for a spectrometer or spectrophotometer of the type wherein one measures the absorbance (A) or percent transmittance (%T) of four different working solutions. One working solution is a blank and the other three working solutions are of the type wherein the amount of cobalt ammonium sulfate present in each of the remaining three solutions varies in an increasing arithmetic progression. This method is characterized in that the above described solution is employed as said working solutions.

Also, the instant invention comprises an improved method for checking photometric accuracy. This method is of the type comprising measuring A or %T of a photometric accuracy test solution at a given wavelength. The method is characterized in that the above solution is employed as the photometric accuracy solution.

Still other features and attendant advantages of the present invention will become apparent to those skilled in the art from a reading of the following detailed description of the preferred embodiments.

DESCRIPTION OF THE PREFERRED EMBODIMENTS

The solution of the instant invention is of the type comprising cobalt ammonium sulfate and sulfuric acid and is characterized in that the sulfuric acid is present in an amount of from about 0.020 to about 0.040 N. Preferably, the solution of the instant invention comprises from about 0.030 to about 0.040 N sulfuric acid. Optimally, the solution of the instant invention comprises from about 0.036 to about 0.038 N sulfuric acid.

The solution of the instant invention can be made by any convenient process known to those skilled in the art. For example, one can add cobalt sulfate and ammonium sulfate to an appropriate vessel. Sulfuric acid of the desired normality is then added to the vessel with mixing to form a solution having the desired concentration of cobalt ammonium sulfate.

The linearity of response checking procedure of the instant invention is of the type which comprises zeroing the spectrometer or spectrophotometer with a suitable blank and then measuring A or %T at a given wavelength of three working solutions comprising cobalt ammonium sulfate and sulfuric acid wherein the cobalt ammonium sulfate present in the three solutions varies in an arithmetic progression. The method of the instant invention is characterized in that the amount of sulfuric acid present in each solution is within the limits set forth above.

The photometric accuracy checking procedure of the instant invention is of the type which comprises zeroing the instrument with a suitable blank and then measuring A or %T of a solution comprising cobalt ammonium sulfate and sulfuric acid at a given wavelength. The method of the instant invention is characterized in that the amount of sulfuric acid present therein is as described above.

The following examples are provided for the purpose of further illustration only and are not intended to be limitations on the disclosed invention.

EXAMPLE 1

The following solutions were prepared:

A. Photometric Zero Solution

Sulfuric acid (20.00 ml) was added to 20 liters of distilled water with mixing to form a uniform solution of 0.037 N $H_2SO_4$.

B. Photometric Level 1 Solution

Cobalt sulfate (35.574 gm) and ammonium sulfate (16.722 gm) were placed in a 2 liter volumetric flask. The Photometric Zero Solution was added to the flask. The flask's contents were mixed until all constituents thereof were completely dissolved. Additional Photometric Zero Solution was added to the volumetric flask in an amount sufficient to yield 2 liters of solution. The contents of the flask were again mixed well.

C. Photometric Level 2 Solution

Cobalt sulfate (41.136 gm) and ammonium sulfate (33.444 gm) were placed in a 2 liter volumetric flask. The Photometric Zero Solution was added to the flask. The flask's contents were mixed well until all constituents thereof were completely dissolved. Additional Photometric Zero Solution was added to the volumetric flask in an amount sufficient to yield 2 liters of solution. The contents of the flask were again mixed well.

D. Photometric Level 3 Solution

Cobalt sulfate (106.700 gm) and ammonium sulfate (50.166 gm) were placed in a 2 liter volumetric flask. The Photometric Zero Solution was added to the flask. The flask's contents were mixed well until all constituents thereof were completely dissolved. Additional Photometric Zero Solution was added to the volumetric flask in an amount sufficient to yield 2 liters of solution. The contents of the flask were again mixed well.

EXAMPLE 2

A BECKMAN Model 42 brand spectrophotometer was turned on and allowed to warm-up to operating temperature. The wavelength was set at 510 nm. Photometric Zero Solution of Example 1 was aspirated into the instrument's flow cell and the instrument was zeroed. The Photometric Zero Solution was removed from the flow cell and an aliquot of the Photometric Level 1 Solution prepared in Example 1 was then aspirated into the flow cell and absorbance was measured. The Photometric Level 1 Solution was removed from the flow cell and Photometric Level 2 Solution of Example 1 was then aspirated and absorbance was again measured. The Photometric Level 2 Solution was removed from the flow cell and the Photometric Level 3 Solution was then aspirated and absorbance was again measured. The data thus obtained was plotted as absorbance versus concentration by the instrument's computer and the results showed that the spectrophotometer was linear.

EXAMPLE 3

A BECKMAN Model 42 brand spectrophotometer was turned on and allowed to warm-up to operating temperature. The wavelength was set at 510 nm. An aliquot of the Photometer Zero Solution prepared in Example 1 was aspirated into the spectrophotometer's flow cell and the spectrophotometer was zeroed. The Photometric Zero Solution was removed from the flow cell and Photometric Level 2 Solution prepared in Example 1 was then aspirated into the flow cell and absorbance was read. The data obtained from this procedure indicated that the spectrophotometer's absorbance reading was within acceptable limits.

Based on this disclosure, many other modifications and ramifications will naturally suggest themselves to those skilled in the art. These are intended to be comprehended as within the scope of this invention.

BIBLIOGRAPHY

1. Frings et al., Clin. Chem., 25(6):1013–1017 (1979).
2. Rand, Clin. Chem., 15:839–863 (1969).
3. Lucas et al., Am. Lab., 9:77–89 (1977).
4. Reule, Appl. Opt., 7:1023–1028 (1968).
5. Frings et al., Clin. Chem., 22:101–102 (1976).

The embodiments of the invention in which an exclusive property or privilege is claimed are defined as follows:

1. A solution of the type comprising cobalt ammonium sulfate and sulfuric acid, characterized in that said sulfuric acid is present therein in an amount from about 0.020 to about 0.040 N.
2. The solution of claim 1 comprising from about 0.030 to about 0.040 N sulfuric acid.
3. The solution of claim 1 comprising from about 0.036 to about 0.038 N sulfuric acid.

* * * * *